United States Patent [19]

Kocher et al.

[11] 4,449,797

[45] May 22, 1984

[54] BINOCULAR OPHTHALMOSCOPE

[76] Inventors: Jakob Kocher, Wiesenweg 19, 7401 Dusslingen; Michael Foerster, Borbeck 23, 4300 Essen 16, both of Fed. Rep. of Germany

[21] Appl. No.: 265,121

[22] Filed: May 19, 1981

[30] Foreign Application Priority Data

May 31, 1980 [DE] Fed. Rep. of Germany ....... 3020750

[51] Int. Cl.$^3$ .............................................. A61B 3/10
[52] U.S. Cl. .................................................. 351/205
[58] Field of Search ............... 351/205, 221, 206, 207, 351/208; 354/6 Z

[56] References Cited

U.S. PATENT DOCUMENTS 3,963,329  6/1976  Stumpf et al. ....................... 351/205

Primary Examiner—John K. Corbin
Assistant Examiner—Rodney B. Bovernick
Attorney, Agent, or Firm—Felfe & Lynch

[57] ABSTRACT

In a binocular ophthalmoscope for indirect observation of an eye to be examined, having an observation unit and an illumination unit connected to the observation unit, wherein the observation unit deflects two closely spaced converging observation beams defining an observation plane with two first and two second mirrors to increase the beam spacing to the interpupillary distance of the observer's eyes. The two first mirrors are mounted closely together between the two second mirrors in a wedge and wherein the illumination unit includes a light source and a third mirror at the emergent side thereof which directs the light issuing from said light source along an illumination beam to the eye to be examined. The first two mirrors are mutually displaceable within the observation unit in the observation plane towards and away from the eyes of the observer to vary the convergence angle of the observation beams and the illumination beam is movable towards and away from said observation plane to vary the angle of the illumination beam with respect thereto.

9 Claims, 4 Drawing Figures

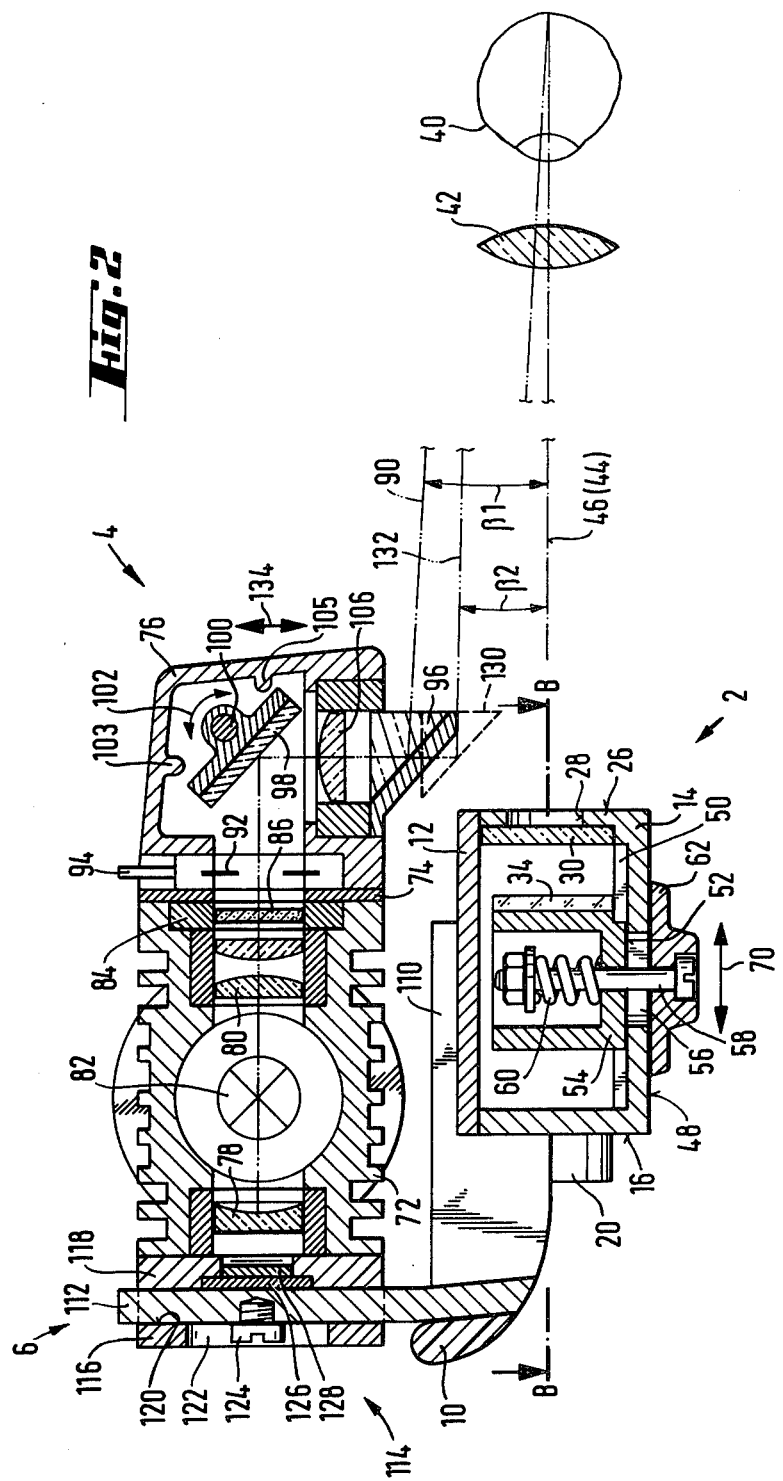

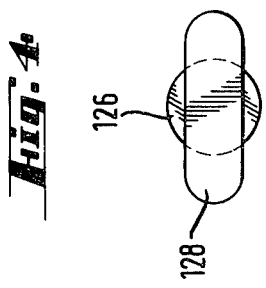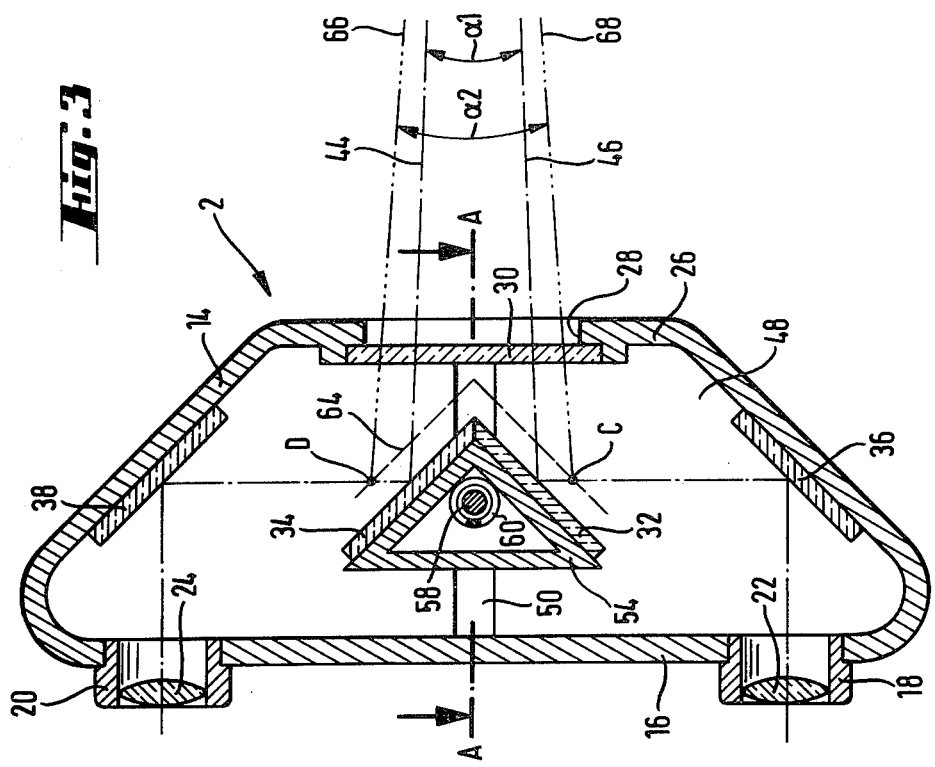

BINOCULAR OPHTHALMOSCOPE

FIELD OF THE INVENTION

This invention relates to a binocular ophthalmoscope for indirect observation, comprising an observation unit and an illumination unit connected to the observation unit by means of connecting means. The said observation unit deflects, with the aid of a first and a second mirror, two observation beams which define an observation plane and which enter the observation unit closely adjacent to one another in such a manner that the spaced relation of the beams is enlarged to the interpupillary distance of the observer's eyes. Both of the first mirrors are disposed closely together between both of the second mirrors to form a wedge and the illumination unit includes a light source and a third mirror at the emergent side which directs the light issuing from the light source along a illumination beam to the eye of the observer.

DESCRIPTION OF THE PRIOR ART

Such an ophthalmoscope is already known (German DOS No. 2,534,784). It serves for binocular observation of the background of an eye to be examined. The observer employs not only the ophthalmoscope, which he wears in front of his eyes, but also an ophthalmoscope lens which is held in front of the eye being examined located at a distance of approximately 50 centimeters from the ophthalmoscope proper.

The illumination beam and both observation beams associated with both of the observer's eyes are directed to the eye being examined. The illumination beam and both observations beams must be separate to enable the ophthalmoscopy to be conducted as free of reflections as possible. However, in order to make binocular observation of the eye at a distance of approximately 50 centimeters or of the virtual image projected by the ophthalmoscope lens possible in spite of the narrowness of the pupilla of the eye being examined, the angle of convergence of both observation beams, i.e. the angle formed by the observation beams which are fixed on one spot of the virtual image, must be reduced. Even while taking this factor into account, however, the largest possible angle of convergence is expedient in order to obtain the best possible stereoscopic image of the retina.

The second mirrors and the associated oculars are adapted to be shifted transversely in the known ophthalmoscope so that the ocular spacing can be adjusted to the observer's interpupillary distance on the one hand and, on the other hand, so that the angle of convergence can be reduced. To this end, both second mirrors and the oculars are pushed farther apart than corresponds to the observer's interpupillary distance. This reduction in the angle of convergence is supposed to make it possible to perform binocular observation of the retina even if the eye to be examined has a very narrow pupilla with a diameter, for instance, of 1 millimeter. The restriction of the observer's field of vision, however, is disadvantageous in the known ophthalmoscope. Moreover, it is provided in the known ophthalmoscope that a third mirror is adapted to pivot about an axis parallel to the observation plane, thus permitting the direction of the illumination beam to be adjusted, thus permitting the direction of the illumination beam to be adjusted. The resultant reduction of ocular reflex, however, is insufficient.

SUMMARY OF THE INVENTION

The object of the present invention is to design an ophthalmoscope of this type such that the most reliable possible ophthalmoscopy is still rendered feasible even under unfavorable conditions, e.g. if the eye to be examined has a narrow pupillar width and a reflex-promoting curvature.

This object is accomplished in accordance with the invention in that the two first mirrors are adapted to be mutually displaced within the observation unit in the observation plane towards and away from the eye of the observer and that the illumination beam is adapted to be moved towards and away from the observation plane.

In the ophthalmoscope in accordance with the invention, both centrally arranged first mirrors can be mutually displaced, thus resulting in a change of the angle of convergence and thus making it possible to adjust the optimum angle of convergence without having to put up with restrictions in the observer's field of vision. Furthermore, operation of the ophthalmoscope is simplified, since only one setting need be made to change the angle of convergence and both oculars together with the associated mirrors need only be moved independently. Due to the fact that the illumination beam is adapted to be moved towards and away from the observation plane, the illumination beam can be positioned so close to the observation plane that adequate light is projected onto the field of examination even if the eye being examined has narrow pupillar widths. The illumination beam can be removed from the observation plane, if the pupillar width permits this, to such an extent that the greatest possible absence of ocular reflex is achieved.

The displaceability of the illumination beam towards and away from the observation plane can be ensured by the fact that the third mirror in the illumination unit is adapted to be moved substantially perpendicular to the observation plane. Preferably, however, the entire illumination unit is displaced relative to the observation unit. It can also be provided that the connecting means has an arm which is mounted on the observation unit, which extends substantially perpendicular to the observation plane and which is displaceably mounted in a guide on the illumination unit. This is advanageous in that it makes displacement easy to execute, since the observer need merely grip the entire illumination unit and shift it.

It can also be provided in an advantageous embodiment of the invention that the third mirror or a fourth mirror disposed in the illumination unit is pivotal about an axis parallel to the observation plane. This makes it possible on the one hand to adjust the direction of the illumination beam so that it can be realigned after being shifted relative to the observation plane, thereby varying the angle between the illumination beam and the observation plane, and on the other hand to include the illumination beam within a certain angular range so that different proportions of the illumination beam bundle can be conveyed to the pupilla of the eye being examined. This makes it possible to reduce the ocular reflex.

The ophthalmoscope in accordance with the invention preferably includes a groove which is formed in the housing of the observation unit and which extends parallel to the bisector of the angle formed by the observation beams, a support on which the two first mirrors are mounted, a projection formed on the support which engages the groove and an operating member which is mounted externally to the observation unit and which is fixedly connected to the support. The groove and the projection on the support of the two first mirrors ensure reliable displacement of the two first mirrors and prevent them from tipping.

Finally, an adjustable diaphragm and a lens can be provided in the illumination unit in an advantageous embodiment of the invention, the diaphragm being arranged in the object-side focal plane of the lens. This construction does not project the filament of the light source onto the pupilla of the eye being examined, but rather the image of the adjustable diaphragm. This results in a considerable absence of reflection in the image of the retina. Moreover, the amount of spurious light can be so reduced, by closing the aperture of the adjustable diaphragm, that ophthalmoscopy is possible even if the eye to be examined is partially clouded.

BRIEF DESCRIPTION OF THE DRAWINGS

Further advantages and features of the invention are revealed in the subclaims and in the following description of the preferred embodiment with reference to the drawings, in which:

FIG. 2 is a simplified illustration of a section through the ophthalmoscope along line A—A in FIG. 3;

FIG. 3 is a simplified illustration of a section along line B—B in FIG. 2; and

FIG. 4 is a view of a member of the connecting means of the ophthalmoscope.

DESCRIPTION OF THE PREFERRED EMBODIMENTS

Figure 1:
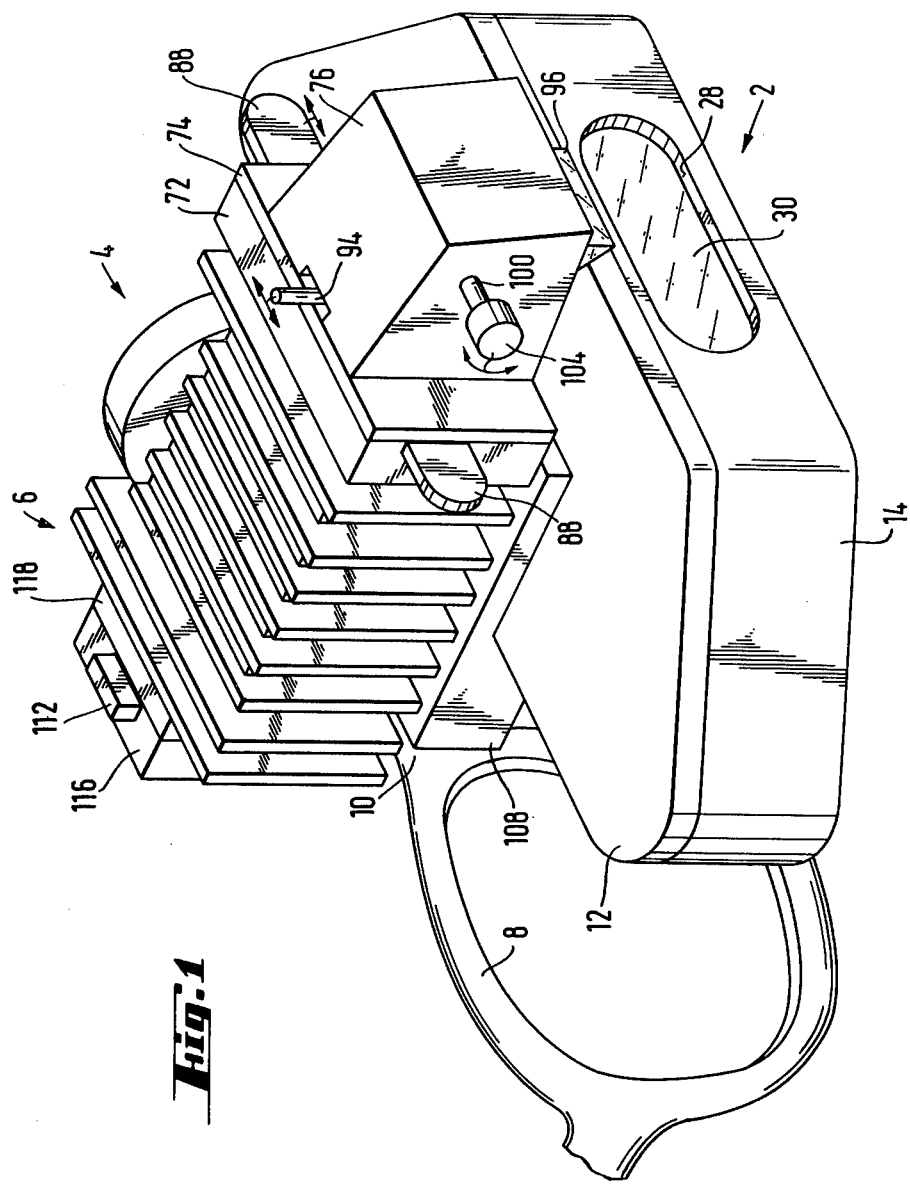
FIG. 1 is a perspective elevation of the preferred embodiment of the binocular ophthalmoscope in accordance with the invention.

The ophthalmoscope illustrated in FIGS. 1-4 includes an observation unit 2 and an illumination unit 4 which are interconnected by connecting means 6. This also makes the connection between the observation unit 2 and the illumination unit 4 on the one hand and a spectacle frame 8 on the other hand, thus enabling the observer to wear the ophthalmoscope like eyeglasses. The connecting means 6 is firmly attached to the spectacle frame 8 adjacent to the bridge 10 in a manner not illustrated (refer to FIG. 2).

The spectacle frame 8 can include conventional correction lenses in the event that the observer is ametropic, i.e. does not have perfect vision. Although the inventive ophthalmoscope is preferably designed as a so-called spectacle ophthalmoscope as illustrated, the observer can also wear the observation unit, the illumination unit 4 and the connecting means 6 with the aid of other means, e.g. a common headband.

The observation unit 2 includes a housing 14 which is closed with the aid of a cover 12 and with two oculars 18 and 20 provided in the rear wall 16 of the housing. The optical axes of the oculars are spaced apart from one another so as to match the observer's interpupillary distance. Although it is possible to mount the oculars 18 and 20 on the housing 14 to enable them to be moved to adjust to the observer's interpupillary distance, it is considered somewhat more expedient in light of practical aspects to fixedly secure the oculars 18 and 20 to the housing 14 and to provide a plurality, e.g. four, observation units featuring different interpupillary distances. In order to provide the observer with accommodationless vision at a distance of approximately 50 centimeters (20 inches), ocular lenses 22 and 24 are provided in the oculars 18 and 20.

An elongated aperture 28 is designed in the front wall 26 of the housing 14 which is parallel to the rear wall 16. This elongated aperture 28 is closed off by a transparent plane glass plate 30. Two first mirrors 32 and 34 are mounted inside the housing 14 in back of the plane glass plate 30 such that their reflecting surfaces form a wedge angle of 90°, the wedge apex faces the plane glass plate 30, and the first mirrors 32 and 34 extend perpendicular to the plane defined by the optical axes of the oculars 18 and 20 and are symmetrically disposed relative to the vertical median plane of the observation unit 2 which coincides with the sectional plane A-A. Second mirrors 36 and 38 are immovably mounted in the housing 14, each of which is parallel to each of the first mirrors 32 and 34 on each of the optical axes of both 18 and 20. When observing an eye 40 to be examined (illustrated schematically in FIG. 2) by means of the ophthalmoscope and ophthalmoscope lens 42, both of the observer's eyes are directed at the eye to be examined or, strictly speaking, at the virtual image produced by the ophthalmoscope lens 42. When both first mirrors 32 and 34 are in the position illustrated in FIG. 3, the observation beams designated as 44 and 46 and associated with both of the observer's eyes proceed as indicated by the dot-and-dash lines. Both observation beams 44 and 46 form an angle of convergence α1. Each of the observation beams 44 and 46 passes through the plane glass plate 30 and is deflected by the first mirror 32 or 34 and by the second mirror 36 or 38 such that the spacing between the observation beams on the observer's side is equal to the observer's interpupillary distance, i.e. the spacing between the optical axes of the oculars 18 and 20. Both observation beams 44 and 46 define the observation plane which in FIG. 3 coincides with the plane of the drawing.

To vary the angle of convergence between the observation beams, in particular to be able to adapt it to a narrower interpupillary distance of the examiner's eye, while on the other hand still keeping it as large as possible to produce optimum stereoscopy, the two first mirrors 32 and 34 are adapted to be moved mutually in the observation plane inside the observation unit 2. A groove 50 is provided in the base 48 of the housing 14 for this purpose. There is displaceably positioned in this groove a projection 52 which is formed on the base of a support 54 to which both of said first mirrors 32 and 34 are secured. The support 54 has the triangular profile which is revealed in the top elevation according to FIG. 3. The groove 50 extends parallel to the observation plane towards the bisectors of the angle formed by both observation beams 44 and 46, i.e. perpendicular to the rear wall 16 of the observation unit 2. A longitudinal slot 56 is formed in the base 48 beneath the groove 50 and extending in same (see FIG. 2). A bolt 58 extends through the longitudinal slot 56 and a hole (not shown) in the base of the support 54. The bolt is supplied with a nut against which a spring 60 biases by means of a spring seat, the other end of the spring 60 biasing against the base of the support 54. The screw head 58 is positioned in a recess in an operating member 52 which is designed as a circular disk and mounted on the outside of the housing base 48. The construction described above causes the support 54 to be flexibly pressed against the inside of the base 48 and the operating member 62 against the outside of the base 48. It is thus possible to move the support 54 and the first mirrors 32 and 34 secured thereto along the groove 50 by means of the operating member 62. The range of movement is defined at the front and back, i.e. to the left and right in FIGS. 2 and 3. by the screw stop 58 at the ends of the longitudinal slot 56. The operating member 62 has a diameter such that it still covers the longitudinal slot 56 when the support 54 is in one of the two extreme positions.

When the support 54 together with the two first mirrors 32 and 34 is moved forward out of the position illustrated in FIGS. 2 and 3 so that the mirror surfaces assume the position 64 indicated by the dotted line in FIG. 3, the observation beams, in this case designated 66 and 68, pass between the first mirrors and the eye to be examined along the lines characterized by the four dots. Due to the enlarged base (the spacing between points C and D), the observation spacing being the same, the observation beams 66 and 68 form an angle of convergence $a2$ which is larger than the angle of convergence $a1$. If the support 54 together with both first mirrors 32 and 34 is moved to the left out of the position illustrated in FIG. 3, the angle of convergence is reduced accordingly. It is thus obvious that the aforecited movement of both first mirrors 32 and 34 varies the angle of convergence between the observation beams, thus optimally adapting the angle of convergence to the respective observation being conducted. It is only necessary to move the operating member 62 frontwards or backwards in the direction indicated by the double arrowhead 70 shown in FIG. 2.

The aperture 28 in the front wall 26 of the housing 14 is so long that vision through the aperture 28 is still unobstructed even at the largest possible angle of convergence.

In practical terms, the observation unit 2 described above is dimensioned such that the angle of convergence can be varied infinitely between 0.86° and 2.64°.

The illumination unit 4 is disposed in the middle above the observation unit 2. It includes a housing segment 72 which is provided with cooling fins and connects to another housing segment 76 via a distance plate 74 at the front, i.e. on the right in FIG. 2. A light source 82 is disposed in the housing segment 72 between a reflector or concave mirror 78, positioned at the left end of the illumination unit 4 in FIG. 2, and a condenser 80. The light source 82 can be designed as a halogen lamp, for example. The electrical connectors of the light source 82 are not shown in the figures. The optical axis of the concave mirror 78 and the condenser 80 extend substantially parallel to the observation plane and thus substantially vertically when the ophthalmoscope is in use so that the entire illumination unit 4 extends predominantly horizontally. This is conducive to a favorable center of gravity for the ophthalmoscope near the spectacle frame 8.

A slide 84 is mounted between the housing segment 72 and the distance plate 74 so as to be displaceable. This slide 84 has one or more color filters which can be selectively moved into the beam path by moving the ends 88 of the slide 84 which project out of the illumination unit 4. The illumination beam is designated 90 in FIG. 2 and is illustrated by a line interrupted by two dots and indicating its central beam. An adjustable diaphragm 92 of the iris diaphragm type is disposed in front of the color filter 86, i.e. to the right of it in FIG. 2. The aperture of the diaphragm can be adjusted by means of a diaphragm adjustment lever 94 which projects from the illumination unit 4.

A third mirror 96 designed as an erecting prism is disposed at the front end and on the underside of the illumination unit 4. It has reflecting surfaces which form an angle of approximately 45° relative to the observation plane defined by the observation beams. The illumination beam is deflected by a fourth mirror 98 disposed in the housing segment 76 in the direction of this third mirror 96. The fourth mirror 98 can be pivoted about a shaft 100 pivotally mounted in the housing segment 76 as indicated by the double arrowhead 102 in FIG. 2. The third 96 and fourth mirrors 98 are aligned such that the illumination beam 90 issuing from the base of the illumination unit 4 is directed towards the eye 40 to be examined and travels in a plane perpendicular to the observation plane and forms the bisectors of the angle between both observation beams 44 and 46.

The shaft 100 projects from the housing segment 76 and has a knob 104 at the free end by means of which the pivotal position of the fourth mirror 98 and thus the direction of the illumination beam 90 can be adjusted. The pivotability of the fourth mirror 98 not only makes it possible to direct the illumination beam 90 towards the eye to be examined, but also to vary the direction of the illumination beam 90 within a range of about 10° such that the examiner's eye is subjected to different proportions of the illumination beam bundle, thus permitting the reflection conditions to be adapted to the eye to be examined. The pivotal range of the fourth mirror 98 is restricted by stops 103 and 105 on the housing structure 76.

A lens 106 is mounted in the illumination beam path in the housing between the third mirror 96 and fourth mirror 98 and is associated with the diaphragm 92 in such a way that the diaphragm 92 is located approximately in the object-side focal plane of the lens 106. The result is that not the light source 82, but rather the diaphragm 92 is projected in the pupil of the eye to be observed. This is the reason for the substantial absence of reflection in the image on the retina. Reducing the adjustable diaphragm 92 can cut down the amount of spurious light in the illumination beam bundle to such an extent that ophthalmoscopy is possible even if the lens of the eye being investigated is partially clouded.

The connecting means 6 between the observation and illumination units 2 and 4 includes two parallel, substantially horizontal arms 108 and 110 to whose front ends of the observation unit 2 is attached. Both arms 108 and 110 are rigidly connected or integrally formed to another arm 122 which is substantially perpendicular to the observation plane and has a constant rectangular cross section in the upper section shown in FIG. 2. The three arms 108, 110 and 112 are affixed to the bridge 10 of the spectacle frame 8 by means of screws (not shown), for example. The connecting means 6 also includes a guide 114 secured to the rear end, i.e. the left end in FIG. 2, of the illumination unit 4 and movably accommodates the arms 112. A groove 120 is designed in the guide 114 between two plates 116 and 118 into which the arm 112 is inserted. A longitudinal slot 122 extending the longitudinal direction of the groove 120 is provided in the plate 116. A cap screw 124 is inserted through the slot and is screwed into the arm 112, thereby restricting together with the longitudinal slot 122 the relative movement between the arm 112 and the guide 114. A circular pressure disk 126 is positioned in the base of the groove 120 formed by the plate 118 which is biased against the arm 112 by a leaf-type spring 128. FIG. 4 is a top view of the pressure disk 126 and spring 128. The pressure disk 126, which the spring 128 flexibly biases against the arm 112, provides a certain amount of resistance opposing the movement of the arm 112 in the guide 114.

The aforedescribed construction of the connecting means 6 makes it possible to move the entire illumination unit 4 vertically upwards and downwards relative to the observation unit 2 and thus the observation plane. This causes the illumination beam path 90 to be shifted towards or away from the observation plane. The third mirror 96 is shown in a position indicated by the dotted line in FIG. 2 in the event that the illumination unit 4 is shifted downwardly out of the position illustrated in FIG. 2. It is obvious that, in so doing, the illumination beam which is designated 132 here, is indicated by the line interrupted by three dots and represents the central beam passes closer to the observation plane defined by observation beams 44 and 46 than does the illustration beam 90. Adjusting the fourth mirror 98 can align the illumination beam 132 with the same spot as the illumination beam 90, the angle $\beta2$ between the illumination beam 132 and the observation plane then being smaller than the angle $\beta1$ between the illumination beam 90 and the observation plane. By shifting the entire illumination unit 4 in the direction of the double arrowhead 134, it is thus possible to vary the spacing between the illumination beam and the observation plane and, in appropriately adjusting the fourth mirror 98, the angle between the illumination beam and the observation plane such that maximum reflection-free ophthalmoscopy is possible even in the case of eyes which have a narrow interpupillary distance while taking the observation conditions into account.

In a practically designed ophthalmoscope, the angle between the illumination beam and the observation plane can be varied between 1.5° and 2.5°, for example.

The invention is not limited to the embodiment described hereinbefore. On the contrary, there are numerous modifications which do not depart from the scope of the invention. Instead of the fourth mirror 98, for example, the third mirror 96 can be designed to pivot about an axis parallel to the observation plane. It is also possible to mount the third mirror 96 in the illumination unit so that it can be moved as indicated by the double arrowhead 134 instead of constructing the entire illumination unit 4 to be displaceable relative to the observation unit 2.

What is claimed is:

1. In a binocular ophthalmoscope for indirect observation of an eye to be examined, the ophthalmoscope having an observation unit, an illumination unit, means for connecting said observation unit to said illumination unit, and means including means for mounting two mirrors in a wedge in said observation unit for reflecting two observation beams from said eye to be examined respectively to the eyes of the observer, said observation beams defining an observation plane, and wherein said illumination unit includes a light source and at least one mirror for directing the light from said light source along an illumination beam to said eye to be examined, the improvement comprising: means for enabling displacement of said means for mounting said two mirrors within said observation unit in said observation plane towards and away form said eyes of said observer and means for enabling movement of said illumination beam towards and away from said observation plane.

2. The ophthalmoscope according to claim 1, wherein said means for enabling movement of said illumination beam comprises means for pivoting at least one said mirror in said illumination unit about an axis parallel to said observation plane.

3. The ophthalmoscope according to claim 2, wherein said means for enabling movement of said illumination beam further comprises another said mirror in said illumination unit movable for directing light from said one mirror along an axis variably close to said observation plane.

4. The ophthalmoscope according to claim 1, wherein said means for enabling movement of said illumination beam comprises means mounting at least one said mirror in said illumination unit for displacement substantially perpendicular to said observation plane.

5. The ophthalmoscope according to claim 1, wherein said means for enabling movement of said illumination beam comprises means in said connecting means mounting said illumination unit for relative displacement substantially perpendicular to said observation plane relative to said observation unit.

6. The ophthalmoscope according to claim 5, wherein said means mounting said illumination unit comprises an arm mounted on one of said observation and illumination units and extending substantially perpendicular to said observation plane and a guide on the other said unit slidably received on said arm.

7. The ophthalmoscope according to claim 6, wherein said means mounting said illumination unit further comprises a spring and a pressure disk which is biased by said spring against said arm in said guide.

8. The ophthalmoscope according to claim 1, wherein said means for enabling displacement comprises a groove in one of said observation unit and means for mounting said two mirrors therein which extends toward and away from said eyes of said observer, a projection on the other thereof which engages said groove, and an operating member which extends externally of said observation unit and which is connected to said means for mounting said two mirrors therein.

9. The ophthalmoscope according to claim 1, further comprising an adjustable diaphragm and a lens in said illumination unit in said illumination beam therefrom, said diaphragm being disposed in the object-side focal plane of said lens.

* * * * *